(12) United States Patent
Valducci

(10) Patent No.: US 7,022,345 B2
(45) Date of Patent: Apr. 4, 2006

(54) ORAL SOLID PHARMACEUTICAL FORMULATIONS WITH PH-DEPENDENT MULTIPHASIC RELEASE

(76) Inventor: Roberto Valducci, Via Sole, 4, 47029 Savignano Sul Rubicone (Forli') (IT)

(*) Notice: Subject to any disclaimer, the term of this patent is extended or adjusted under 35 U.S.C. 154(b) by 0 days.

(21) Appl. No.: 09/898,425

(22) Filed: Jul. 3, 2001

(65) Prior Publication Data

US 2002/0034541 A1     Mar. 21, 2002

(30) Foreign Application Priority Data

Jul. 14, 2000   (IT)   ................... MI2000A1603

(51) Int. Cl.
*A61K 9/14*   (2006.01)
*A61K 9/20*   (2006.01)
*A61K 9/22*   (2006.01)
*A61K 9/48*   (2006.01)

(52) U.S. Cl. .............. 424/489; 424/464; 424/465; 424/468; 424/451; 424/486

(58) Field of Classification Search ............ 424/400, 424/472, 489, 451, 465, 490, 497, 458, 464, 424/457, 469, 468, 474, 486
See application file for complete search history.

(56) References Cited

U.S. PATENT DOCUMENTS

| 4,713,248 | A | * | 12/1987 | Kjornaes et al. | ......... | 424/469 |
| 5,482,718 | A | * | 1/1996 | Shah et al. | ......... | 424/480 |
| 5,725,880 | A | * | 3/1998 | Hirakawa et al. | ......... | 424/480 |
| 5,889,028 | A | * | 3/1999 | Sandborn et al. | ......... | 514/343 |
| 5,914,132 | A |   | 6/1999 | Kelm et al. |   |   |
| 5,972,373 | A | * | 10/1999 | Yajima et al. | ......... | 424/439 |
| 6,160,107 | A | * | 12/2000 | Ishizuka et al. | ......... | 514/563 |
| 6,228,396 | B1 | * | 5/2001 | Watts | ......... | 424/463 |
| 6,500,457 | B1 | * | 12/2002 | Midha et al. | ......... | 424/464 |

FOREIGN PATENT DOCUMENTS

| EP | 0453001 | 10/1991 |
| NZ | 221223 | 12/1989 |
| NZ | 232029 | 4/1992 |
| NZ | 235319 | 3/1993 |
| WO | WO 96/04918 | 2/1996 |
| WO | WO 97/28801 | 8/1997 |
| WO | WO 99/06027 | 2/1999 |

OTHER PUBLICATIONS

Khan et al. (A pH-dependent colon targeted oral delivery system using methacrylic acid copolymers 1. Manipulation of drug release using EUDRAGIT L100-55 and EUDRAGIT S100 combinations, J. of Controlled Release, 58, (1999) pp 215-222).*

M. Zahirul I. Khan, et al, A pH-Dependant Colon-Targeted Oral Drug Delivery System Using Methacrylic Acid Copolymers II. Manipulation of Drug Release Using Eudragit® L100 and Eudragit S100 Combinations, Drug Development and Industrial Pharmacy, vol. 26, No. 5, 2000, pp. 549-554.

Zhaopeng Hu, et al, Technology to Obtain Sustained Release Characteristics of Drugs after Delivered to the Colon, Journal of Drug Targeting, vol. 6, No. 6, 1999, pp. 439-448.

* cited by examiner

*Primary Examiner*—Thurman K. Page
*Assistant Examiner*—Blessing Fubara
(74) *Attorney, Agent, or Firm*—William J. Sapone; Henry Coleman; R. Neil Sudol

(57) ABSTRACT

Oral solid pharmaceutical compositions with pH-dependent multiphasic release, containing, as active ingredient, a molecule useful in the inflammatory bowel disease therapy, are described, being such compositions suitable to the release of the active ingredient in the intestinal tract.

9 Claims, No Drawings

ORAL SOLID PHARMACEUTICAL FORMULATIONS WITH PH-DEPENDENT MULTIPHASIC RELEASE

TECHNICAL FIELD

Oral solid pharmaceutical formulations with pH-dependent multiphasic release, containing, as active ingredient, a molecule useful in the inflammatory bowel disease therapy.

BACKGROUND OF THE INVENTION

The ulcerative colitis is a chronic inflammatory form of the colon mucosa; in particular, the inflammatory reaction concerns the large intestine, i.e. the colon with localization in the terminal tract, the rectum and the sigmoid flexure, while the ileum is only seldom involved. In the most serious cases the inflammation can spread to the submucosa.

Crohn's disease or granulomatous colitis is a manifestation of inflammatory type, which usually affects the small intestine, the jejunum and the whole colon, including also the rectum. This inflammatory reaction differs from the ulcerative colitis as, normally, involves deeper layers of the mucosa.

The differential diagnosis between ulcerative colitis and Crohn's disease is often problematic, so that the international medical literature frequently uses the common term "Inflammatory Bowel Disease" (IBD) to jointly indicate these pathologies.

The therapeutic approach in the various forms of the IBD includes the use of corticosteroids such as prednisone, prednisolone or hydrocortisone, above all in the acute attacks, together with the administration of liquids, plasma and electrolytes.

For the treatment of the forms from slight-moderate to chronic IBD, in the past, sulfasalazine was commonly used, whose mechanism of action is not completely well-known: sulfasalazine, orally administered, reaches unmodified the colon, where it is transformed by the resident bacteria into sulfapyridine and mesalazine.

Today mesalazine is commonly accepted as the pharmacologically active moiety of sulfasalazine, while sulfapyridine would have just the role of carrier, bringing the active moiety at the site of action.

Sulfapyridine is not free of toxicity and the intolerance toward such molecule is frequent; therefore, in the last years, much interest has been addressed to the utilization of mesalazine as active ingredient for the treatment of the forms from slight-moderate to chronic IBD.

The oral administration of mesalazine is made nevertheless problematic by the fact that such drug is almost completely absorbed in the small intestine and, therefore, just a small amount reaches the colon to carry on the therapeutic action. With the aim of overcoming such difficulty, during the past, formulations of mesalazine with particular coatings were developed, exhibiting the characteristic to release the active ingredient only in the desired area, also to avoid systemic side effects. These pharmaceutical compositions are retard, or slow release, forms, suitable to prevent or delay the absorption of mesalazine in the proximal tract to obtain therapeutic concentrations in the ileum and colon.

The most wide-spread formulations available on the pharmaceutical market are pH-dependent, time-dependent or bacterium-dependent.

Document EP 0 040 590 (Aktiebolaget Hassle) describes oral pharmaceutical preparations able to release a drug, for example mesalazine, selectively in the colon, starting from pH 5.5.

This is obtained through a coating of the active ingredient with a mixture of an acrylic anionic polymer soluble just at pH 5.5, such as, for example, Eudragit L, in quantities ranging from 10 to 85%, and an acrylic polymer substituted by quaternary ammonium, insoluble in water, like, for example, Eudragit RS or RL, in quantities ranging from 15 to 90%. In these formulations the selective release of the active ingredient in the intestine is obtained through the utilization of a polymer having a pH-dependent solubility. The blending with one or more polymers having a pH-independent solubility prevents the active ingredient from being released too rapidly, once reached the pH of solubilization.

Document EP 0 097 651 (J. B. Tillott Ltd.) regards a solid oral dosage form, for example a capsule or a tablet, containing a pharmacologically active agent, for example mesalazine, for the treatment of colon pathologies. Such solid form is coated with an anionic polymer, insoluble up to pH 7.

Document EP 0 572 486 (J. B. Tillott Ltd.) claims an oral dosage form suitable to dose <selectively a drug in the intestine, including a plurality of granules of active ingredient contained in a capsule. Both the granules and the capsule are coated with equal or different materials, soluble in the intestine, in the ileum or colon, depending on the coating, and this allows a more gradual release of mesalazine in the colon, avoiding, in this way, possible local irritations due to a too rapid release. Preferably, the coating of the pharmaceutical forms is composed by polymers that start dissolving at pH $\geq 7$.

Document IT 1246382 (Eurand International S.p.A.) includes several controlled release oral formulations. In particular, it describes compositions coated with a polymer, for example, Eudragit S, which starts slowly dissolving at pH 6.2, applied onto a second polymeric layer, for example ethylcellulose, to provide a release of the active ingredient at pH 7.2. To obtain the desired effect the two membranes have to be applied in a sequence, otherwise, coating the active ingredient with a mixture of the two components, the dissolution of the solid form in the colon turns out to be too rapid.

Document EP 0 629 398 (Tanabe Seiyaku Co. Ltd.) refers to pharmaceutical preparations able to provide a controlled release of the active ingredient in the desired zone of the intestinal tract (duodenum, small intestine, colon, rectum), and anyway at a pH $\geq 5$, through a proper choice of the coating, and checking, furthermore, the dissolution speed of the drug itself. Among the many coatings indicated as useful, Eudragit L and Eudragit S are mentioned.

All the above described formulations have in common the characteristic to start the dissolution of the coating layer at a pH >5–6, but the real release of the active ingredient occurs either slowly at a pH higher than 6–6.5, or in a rapid way at a pH higher than 7.

The above mentioned patents are based on the use of a polymer having a solubility depending on the pH: when the formulation reaches intestinal regions having pH values in which the polymer is soluble, the liberation of mesalazine begins, which can be very rapid or delayed in case the formulation contains also polymers with a pH-independent solubility. It is nevertheless very difficult with these formulations to obtain the homogeneous distribution of the active ingredient in the area affected by the inflammatory reaction.

It is therefore necessary to develop new pharmaceutical formulations suitable to assure a uniform release of mesalazine in all the intestinal regions target of the therapeutic action.

SUMMARY OF THE INVENTION

It has been now found out that it is possible to obtain a uniform release of an active ingredient in all the intestine area hit by IBD by means of pharmaceutical formulations in which polymers or mixtures of different polymers are associated, each one soluble starting from a pH value different from the others and ranging from 6 to 7.

Such pharmaceutical formulations are able to release active ingredients in a pH-dependent multiphasic way, i.e. in more portions with a controlled amount depending on the pH.

DESCRIPTION OF THE INVENTION

Oral solid formulations are the object of the present invention, containing, as active ingredient, a molecule useful in the IBD therapy, characterized by the association of different polymers or mixtures of polymers, each one soluble starting from a pH value different from the others and ranging from 6 to 7.

Such formulations release the active ingredient in a multiphasic way, each phase occurring at a different pH value ranging from 6 to 7.

Particularly preferred is the association of three polymers or mixtures of polymers, soluble starting from a pH value different one from the other and ranging from 6 to 7, which causes a triphasic release of the active ingredient. Preferred is the combination of a polymer or a mixture of polymers soluble starting from pH 6, a polymer or a mixture of polymers soluble starting from pH 6.5 and a polymer or a mixture of polymers soluble starting from pH 7. In this case the active ingredient is released by the invention formulations in a triphasic way, preferably in the following pH-dependent quantities:

| pH = 6   | ⇒ | 10–60% | of the released active ingredient  |
| pH = 6.5 | ⇒ | 10–60% | of the released active ingredient  |
| pH = 7   | ⇒ | 10–60% | of the released active ingredient. |

Even more preferably the active ingredient release occurs in the following pH-dependent quantities:

| pH = 6   | ⇒ | 30–35% | of the released active ingredient  |
| pH = 6.5 | ⇒ | 30–35% | of the released active ingredient  |
| pH = 7   | ⇒ | 30–35% | of the released active ingredient. |

The invention formulations are particularly suitable to the mesalazine administration. They can, furthermore, be utilized for the administration of other active ingredients useful in the IBD therapy, among which to be mentioned are steroids, such as prednisone, prednisolone or budenoside, antibiotics and anti-inflammatories.

The formulations of this invention can be in the form of capsules containing micro-tablets, tablets, granules or microgranules or pellets, or in the form of multilayer tablets, or in the form of sachets or dispensers containing granules or microgranules or pellets. With the term micro-tablet we identify a tablet having a diameter equal or inferior to 2 mm.

Each capsule contains micro-tablets, tablets, granules or microgranules or pellets of three types, each one presenting a coating including a polymer soluble starting from a pH value ranging from 6 to 7, such pH value being different for each one of such three types.

Similarly, granules or microgranules or pellets of three types are dosable in sachets or dispensers for granules.

Preferably such coating contains from 20 to 100% of said polymer or mixture of polymers. Such coating can include also a fatty acid at 10–20 carbon atoms, preferably stearic acid, usually in a quantity ranging from 0 to 40% and a pharmaceutically acceptable plasticizer, preferably diethylphtalate, usually in a quantity ranging from 0 to 40%.

Preferably in each capsule or sachet such three types are contained in proportions suitable to obtain the above described triphasic release profiles; the best ratio is 1:1:1.

According to a particularly preferred application, in each capsule, one third of such micro-tablets, tablets, granules or microgranules or pellets exhibits a coating including a polymer or a mixture of polymers soluble starting from pH 6, another third includes a coating constituted of a polymer or a mixture of polymers soluble starting from pH 6.5 and the last third presents a coating including a polymer or a mixture of polymers soluble starting from pH 7.

Preferably, the polymer soluble starting from pH 6 is Eudragit L or cellulose acetatephtalate, or Hydroxypropylmethylcellulosephtalate or Hydroxypropylmethyl-cellulose-acetatesuccinate type L.

The mixture of polymers soluble starting from pH 6.5 is Eudragit L or Hydroxypropylmethylcellulosephtalate or Hydroxypropylmethyl-celluloseacetatesuccinate type L in a mixture 1:1 with Eudragit S.

The polymer soluble starting from pH 7 is Eudragit S or Hydroxypropylmethylcelluloseacetatesuccinate type M.

The above mentioned granules or microgranules or pellets are constituted of the active ingredient and pharmaceutically acceptable excipients, commonly used in the preparation of granules; their preparation happens by processes of granulation, nucleation, layering, extrusion and spheronization, that are well-known to the experts of modified release oral dosage forms.

The above micro-tablets and tablets are made up of the active ingredient and pharmaceutically acceptable excipients commonly used in the preparation of tablets. They can optionally include also from 5 to 35% of a polymer or a mixture of polymers soluble at a pH ranging from 6 to 7, from 0 to 10% of a fatty acid at 12–20 carbon atoms, preferably stearic acid, and from 0 to 10% of a pharmaceutically acceptable plasticizer, preferably diethylphtalate. In this case, the polymer or mixture of polymers contained in the micro-tablets or in the tablets is the same as that included in their coating.

Alternatively, the invention formulation can be in the form of multilayer tablets: these are made up of three layers, each one including, besides the active ingredient and the excipients commonly utilized for the preparation of tablets, a polymer or mixture of polymers soluble starting from a pH value ranging from 6 to 7 and different from the one in which the polymer or the mixture of polymers of the other two layers dissolves.

Preferably each tablet contains from 5 to 35% of polymer. Optionally, such tablets can contain also a fatty acid at 12–20 carbon atoms, preferably stearic acid, usually in a quantity ranging from 0 to 10% and a pharmaceutically acceptable plasticizer, preferably diethylphtalate, commonly in a quantity ranging from 0 to 10%.

Preferably such layers contain amounts of the active ingredient suitable to obtain the above described triphasic release profiles; preferably the quantities of active ingredient in the three layers are equal.

According to a particularly preferred application, the internal layer includes a polymer or a mixture of polymers soluble starting from pH 7, one of the external layer includes a polymer or a mixture of polymers soluble starting from pH 6.5 and the second external layer includes a polymer or a mixture of polymers soluble starting from pH 6. Preferably such polymer soluble starting from pH 6 is Eudragit L or cellulose acetatephtalate, the mixture of polymers soluble starting from pH 6.5 is a mixture 1:1 of Eudragit L/Eudragit S and the polymer soluble starting from pH 7 is Eudragit S.

The multilayer tablets present furthermore a coating preferably including a polymer or a mixture of polymers soluble starting from pH 6.0, like, for example, Eudragit L. Optionally such coating includes also a fatty acid at 12–20 carbon atoms, preferably stearic acid, and/or a plasticizer, preferably diethylphtalate. Preferably such coating contains from 20 to 100% of said mixture of polymers, from 0 to 40% of fatty acid and from 0 to 40% of diethylphtalate.

In case the active ingredient is mesalazine, the formulation is prepared having a dosage ranging from 100 to 3000 mg.

Sachets and dispensers for granules or microgranules or pellets contain a mesalazine dosage ranging from 100 and 3000 mg.

EXAMPLE 1

4 Kg of mesalazine have been granulated on a fluid bed with tangential insert. The active ingredient powder has been sprayed with ethanol or with a mixture 1:1 of water/ethanol containing PVP at 20%. The granules have been selected with a net of 1200 μ and the not conform fraction has been micronized, suspended in water/ethanol 1:1 and applied on the granules.

The so obtained granules have been transferred into desiccator and then tested to check the potency and the dissolution rate, obtaining the results reported in Table 1.

The dissolution tests of Table 1 and of the following tables have been carried out with Paddle Apparatus, USP.

TABLE 1

| Mesalazine content | Dissolution (1 hour in HCl 0.1N) | Dissolution (1 hour in tampon pH 6.0) |
|---|---|---|
| >950 mg/g | >90% | >90% |

EXAMPLE 2

2.1) 500 g of granulate of Example 1 have been coated, in two steps, with 600 g of an ethanolic solution containing 7% p/p of Eudragit S, 8.4 g of diethylphtalate and 9 g of stearic acid, utilizing a fluid bed equipped with bottom spraying insert. For the first coating 400 g of the indicated solution have been utilized; the remaining quantity has been applied in a second coating. After each coating step the granules have been dried prior to being tested. The dissolution tests have provided the results reported in Table 2.

TABLE 2

| Time | Medium | % dissolution after $1^{st}$ coating | % dissolution after $2^{nd}$ coating |
|---|---|---|---|
| $1^{st}$ hour | HCl 0.1N | n.d. | n.d. |
| $2^{nd}$ hour | HCl 0.1N | 0.71% | 4.1% |
| $3^{rd}$ hour | Tampon pH 6.0 | 98.7% | 4.6% |
| $4^{th}$ hour | Tampon pH 6.5 | — | 7.0% |
| $6^{th}$ hour | Tampon pH 7.0 | — | 97.5% |

2.2.) 500 g of product manufactured according to Example 1 have been coated in a fluid bed with bottom spraying insert with 600 g of an ethanolic solution containing: 7% p/p of Eudragit L, 8.4 g of diethylphtalate and 9 g of stearic acid. The granules obtained have been dried and tested: the dissolution data obtained are summarized in Table 3.

TABLE 3

| Time | Medium | % dissolution |
|---|---|---|
| $1^{st}$ hour | HCl 0.1N | 3.79% |
| $2^{nd}$ hour | HCl 0.1N | 5.78% |
| $3^{rd}$ hour | Tampon pH 6.0 | 91.9% |
| $4^{th}$ hour | Tampon pH 6.5 | — |
| $6^{th}$ hour | Tampon pH 7.0 | — |

2.3) 500 g of granulate of Example 1 have been coated with 600 g of a solution containing 7% p/p of a mixture 1:1 of Eudragit L and Eudragit S, 8.4 g of diethylphtalate and 9 g of stearic acid, in a fluid bed equipped with bottom spraying insert. The granules obtained have been dried and tested, obtaining the results reported in Table 4.

TABLE 4

| Time | Medium | % dissolution |
|---|---|---|
| $1^{st}$ hour | HCl 0.1N | 0.41% |
| $2^{nd}$ hour | HCl 0.1N | 2.20% |
| $3^{rd}$ hour | Tampon pH 6.0 | 17.6% |
| $4^{th}$ hour | Tampon pH 6.5 | 98.9% |
| $6^{th}$ hour | Tampon pH 7.0 | — |

2.4) The granules manufactured as described in Examples 2.1, 2.2. and 2.3 have been mixed in the ratio 1:1:1 and inserted into capsules in a quantity corresponding to 400 mg of mesalazine for each capsule. The capsules have been tested to evaluate the mesalazine dissolution profile: the results are reported in Table 5.

TABLE 5

| Time | Medium | % dissolution |
|---|---|---|
| $2^{nd}$ hour | HCl 0.1N | 8.20% |
| $3^{rd}$ hour | Tampon pH 6.0 | 31.7% |
| $4^{th}$ hour | Tampon pH 6.5 | 58.9% |
| $6^{th}$ hour | Tampon pH 7.0 | 94.1% |

EXAMPLE 3

In a high speed granulator 8 Kg of mesalazine have been wetted with 1.2 Kg of a polyvinylpyrrolidone binder solution at 20% in ethanol and processed to obtain granules having high density and low friability. The granules having granulometry between 500 and 1000 microns have been selected; the granules with a granulometry not included in said interval have been micronized, suspended in water/ethanol 1:1 and applied on the fraction of 500–1000 microns. The so obtained granules have been divided into three portions and each of these portions has been coated separately in a fluid bed as described in the following example.

EXAMPLE 4

4.1) 2.5 Kg of granules obtained in Example 3 have been transferred in a fluid bed and coated with 3.0 Kg of the ethanolic solution of Eudragit S utilized in the Example 2.1. The product obtained has been dried and tested to check the mesalazine release profile. The results obtained in the dissolution test are reported in Table 6.

TABLE 6

| Time | Medium | % dissolution |
| --- | --- | --- |
| 1$^{st}$ hour | HCl 0.1N | 0.11% |
| 2$^{nd}$ hour | HCl 0.1N | 1.50% |
| 3$^{rd}$ hour | Tampon pH 6.0 | 1.80% |
| 4$^{th}$ hour | Tampon pH 6.5 | 63.9% |
| 6$^{th}$ hour | Tampon pH 7.0 | 103.8% |

4.2) 2.5 Kg of granules obtained in Example 3 have been transferred in a fluid bed and coated with 3.0 Kg of the ethanolic solution of Eudragit L utilized in the Example 2.2. In Table 7 the results of the dissolution test are reported.

TABLE 7

| Time | Medium | % dissolution |
| --- | --- | --- |
| 2$^{nd}$ hour | HCl 0.1N | 8.5% |
| 3$^{rd}$ hour | Tampon pH 6.0 | 74.9% |
| 4$^{th}$ hour | Tampon pH 6.5 | 96.1% |
| 6$^{th}$ hour | Tampon pH 7.0 | 100.1% |

4.3) 2.4 Kg of granules obtained in Example 3 have been transferred in a fluid bed and coated with 3 Kg of the ethanolic solution of Eudragit S and Eudragit L utilized in the Example 2.3. The granules obtained have been dryed and tested. In Table 8 the dissolution test results are reported.
4.4)

TABLE 8

| Time | Medium | % dissolution |
| --- | --- | --- |
| 1$^{st}$ hour | HCl 0.1N | 0.32% |
| 2$^{nd}$ hour | HCl 0.1N | 4.70% |
| 3$^{rd}$ hour | Tampon pH 6.0 | 21.2% |
| 4$^{th}$ hour | Tampon pH 6.5 | 97.7% |
| 6$^{th}$ hour | Tampon pH 7.0 | 98.6% |

4.4) The granules coated according to the above Examples 4.1, 4.2 and 4.3 have been mixed in the ratio 1:1:1 and inserted into capsules in a quantity corresponding to 500 mg of mesalazine/capsule. The so obtained capsules have been tested to evaluate the mesalazine release profile. The results obtained in the dissolution test are reported in Table 9.

TABLE 9

| Time | Medium | % dissolution |
| --- | --- | --- |
| 2$^{nd}$ hour | HCl 0.1N | 6.4% |
| 3$^{rd}$ hour | Tampon pH 6.0 | 33.2% |
| 4$^{th}$ hour | Tampon pH 6.5 | 84.5% |
| 6$^{th}$ hour | Tampon pH 7.0 | 92.3% |

EXAMPLE 5

3 Kg of mesalazine have been granulated with 0.8 Kg of a solution at 20% of polyethylene glycol 4000 in ethanol/water 1:2 and the resulting granulate has been extruded and spheronized to obtain granules with an average diameter of 1200 μ. The so obtained granules, coated as described in the examples 4.1, 4.2 and 4.3, have been mixed in the ratio 1:1:1 and inserted into capsules in a quantity corresponding to 500 mg of mesalazine/capsule. The so obtained capsules have shown the dissolution profile reported in Table 10.

TABLE 10

| Time | Medium | % dissolution |
| --- | --- | --- |
| 2$^{nd}$ hour | HCl 0.1N | 4.3% |
| 3$^{rd}$ hour | Tampon pH 6.0 | 30.3% |
| 4$^{th}$ hour | Tampon pH 6.5 | 80.3% |
| 6$^{th}$ hour | Tampon pH 7.0 | 93.0% |

EXAMPLE 6

In a high speed granulator 4 Kg mesalazine have been wetted with 0.600 Kg of a polyvinylpyrrolidone binder solution at 20% in ethanol and granulated to have high density and low friability granules.

The granules having granulometry between 150–400 microns have been selected; the granules having granulometry not included in this interval have been micronized and regranulated. The so obtained granules have been divided in three portions and each of such portions has been coated separately in a fluid bed as described in the following Example.

EXAMPLE 7

7.1) 0.800 Kg of the granules obtained in the Example 6 have been transferred in a fluid bed and coated with 1.5 Kg of the Eudragit S ethanolic solution utilized in the Example 2.1. The product obtained has been desiccated and tested to evaluate the mesalazine release profile. The results of the dissolution test are reported in Table 11.

TABLE 11

| Time | Medium | % dissolution |
| --- | --- | --- |
| 1$^{st}$ hour | HCl 0.1N | 0.21% |
| 2$^{nd}$ hour | HCl 0.1N | 3.5% |
| 3$^{rd}$ hour | Tampon pH 6.0 | 5.1% |
| 4$^{th}$ hour | Tampon pH 6.5 | 66.4% |
| 6$^{th}$ hour | Tampon pH 7.0 | 100% |

7.2) 0.800 Kg of the granules obtained in the Example 6 have been transferred in a fluid bed and coated with 1.5 Kg of the Eudragit L ethanolic solution utilized in the Example 2.2. In Table 12 are reported the results of the dissolution test.

TABLE 12

| Time | Medium | % dissolution |
|---|---|---|
| 1st hour | HCl 0.1N | 1.4% |
| 2nd hour | HCl 0.1N | 7.2% |
| 3rd hour | Tampon pH 6.0 | 73.8% |
| 4th hour | Tampon pH 6.5 | 98% |
| 6th hour | Tampon pH 7.0 | 102.3% |

7.3) 0.008Kg of the granules obtained in the Example 6 have been transferred in a fluid bed and coated with 1.5 Kg of the Eudragit S and Eudragit L ethanolic solution utilized in the Example 2.3. The granules obtained have been desiccated and tested. In Table 13 are reported the results of the dissolution test.

TABLE 13

| Time | Medium | % dissolution |
|---|---|---|
| 1st hour | HCl 0.1N | 0.20% |
| 2nd hour | HCl 0.1N | 1.2% |
| 3rd hour | Tampon pH 6.0 | 23.6% |
| 4th hour | Tampon pH 6.5 | 93.4% |
| 6th hour | Tampon pH 7.0 | 100.4% |

7.4) The granules coated according to the above examples 7.1, 7.2 and 7.3, have been mixed in the ratio 1:1:1; the so obtained mixture has been dosed in monodose sachets containing 1200 mg mesalazine per sachet; the so obtained sachets have been tested to evaluate the mesalazine release profile. The results obtained in the dissolution test are reported in Table 14.

TABLE 14

| Time | Medium | % dissolution |
|---|---|---|
| 1st hour | HCl 0.1N | 1.0% |
| 2nd hour | HCl 0.1N | 4.2% |
| 3rd hour | Tampon pH 6.0 | 34.4% |
| 4th hour | Tampon pH 6.5 | 86.1% |
| 6th hour | Tampon pH 7.0 | 102.1% |

EXAMPLE 8

The following granulates, suitable to the tablet manufacture, have been prepared by means of a high speed granulator:

8.1) 8 Kg of mesalazine, 1.3 Kg of Eudragit S and 0.3 Kg of stearic acid, micronized, have been granulated adding 1 Kg of an ethanolic solution containing 10% p/p of Eudragit S and 0.03 Kg of diethylphtalate.

8.2) Such granulate has been prepared as described in the Example 8.1, utilizing the following substances and relative quantities:

| Mesalazine | 8 Kg |
|---|---|
| Eudragit L | 1.3 Kg |
| Stearic Acid | 0.3 Kg |

1 Kg of binder solution containing:

| Eudragit L in ethanol | 10% p/p |
|---|---|
| Diethylphtalate | 0.03 Kg |

8.3) Such granulate has been prepared with the same procedure utilized in the Example 8.1, using the following substances and relative quantities:

| Mesalazine | 8 Kg |
|---|---|
| Eudragit S | 0.65 Kg |
| Eudragit L | 0.65 Kg |
| Stearic Acid | 0.30 Kg |

1 Kg of binder solution containing:

| Eudragit S in ethanol | 5% p/p |
|---|---|
| Eudragit L in ethanol | 5% p/p |
| Diethylphtalate | 0.03 Kg |

EXAMPLE 9

9.1) 1.020 Kg of granulate of Example 8.1 have been mixed with 30 g of magnesium stearate and pressed with round punches of 6 mm of diameter to obtain tablets having an average weight of 175 mg. A quantity equal to 950 g of so obtained tablets has been film-coated in a rotating pan utilizing an ethanolic solution containing 7% p/p of Eudragit S, 2.2% p/p of diethylphtalate and 2% p/p of stearic acid. The film-coating process has been stopped when it has been reached a weight increase per each tablet of 10 mg.

9.2) 1.020 Kg of granulate of Example 8.2 have been utilized to prepare tablets as described in Example 9.1, which have been filmed in a rotating pan utilizing 800 g of an ethanolic solution containing 7% p/p Eudragit L, 2.2% diethylphtalate and 2% stearic acid. The film-coating process has been protracted up to the obtainment of a weight increase per each tablet of 10 mg.

9.3) 1.020 Kg of granulate of Example 8.3 have been utilized to prepare tablets as described in Example 9.1, which have been then film-coated in a rotating pan utilizing 800 g of an ethanolic solution containing 7% p/p of a mixture 1:1 of Eudragit S and Eudragit L, 2.2% of diethylphtalate and 2% of stearic acid.

9.4) The tablets obtained in the examples 9.1, 9.2 and 9.3 have been inserted into gelatin capsules size "0" in the following quantities:
1 tablet containing Eudragit S (Example 9.1)
1 tablet containing Eudragit L (Example 9.2)
1 tablet containing Eudragit L +S (Example 9.3)
The mesalazine release profile from the so prepared capsules has been analyzed through dissolution tests, obtaining the results reported in Table 15.

TABLE 15

| Time | Medium | % dissolution |
|---|---|---|
| 2nd hour | HCl 0.1N | 0.5% |
| 3rd hour | Tampon pH 6.0 | 22.6% |

TABLE 15-continued

| Time | Medium | % dissolution |
|---|---|---|
| 4$^{th}$ hour | Tampon pH 6.5 | 50.1% |
| 6$^{th}$ hour | Tampon pH 7.0 | 87.0% |

EXAMPLE 10

A new granulate has been prepared putting into a granulator 4.0 Kg of mesalazine wetted with 600 g of a polyvinylpyrrolidone binder solution at 20% in ethanol.

The so obtained granules have been mixed with 80 g of magnesium stearate and pressed to obtain micro-tablets, 2 mm in diameter, and average weight of about 6 mg.

10.1) 500 g of the so obtained micro-tablets have been film-coated in a fluid bed with 600 g of an ethanolic solution containing 7% of Eudragit S, 8.4 g of diethylphtalate and 9 g of stearic acid.

10.2) 500 g of the micro-tablets obtained have been treated as described in the Example 10.1 with 600 g of an ethanolic solution containing 7% of Eudragit L, 8.4 g of diethylphtalate and 9 g of stearic acid.

10.3) 500 g of the above obtained tablets have been treated as described in the Example 10.1 with 600 g of an ethanolic solution containing 7% of a mixture 1:1 of Eudragit L and Eudragit S, 8.4 g of diethylphtalate and 9 g of stearic acid.

10.4) The tablets obtained as described in the Examples 10.1, 10.2 and 10.3 have been mixed between them in the ratio 1:1:1 and inserted into capsules in a quantity equal to 800 mg of mesalazine. The results obtained by the dissolution test on the so obtained capsules are reported in Table 16.

TABLE 16

| Time | Medium | % dissolution |
|---|---|---|
| 2$^{nd}$ hour | HCl 0.1N | 6.7% |
| 3$^{rd}$ hour | Tampon pH 6.0 | 30.8% |
| 4$^{th}$ hour | Tampon pH 6.5 | 65.1% |
| 6$^{th}$ hour | Tampon pH 7.0 | 93.3% |

EXAMPLE 11

2.5 Kg of mixture of granules and magnesium stearate of Example 10 have been pressed to obtain tablets with a diameter of 6 mm and an average weight equal to about 140 mg.

11.1) 700 g of such tablets have been coated with the solution described in Example 10.1 up to the obtainment of a weight increase equal to about 13 mg per tablet.

11.2) 700 g of such tablets have been coated with the solution described in Example 10.2 up to the obtainment of a weight increase equal to about 13 mg per tablet.

11.3) 700 g of such tablets have been coated with the solution described in Example 10.3 up to the obtainment of a weight increase equal to about 13 mg per tablet.

11.4) The tablets obtained as described in the examples 11.1, 11.2 and 11.3 have been inserted in the ratio 1:1:1 into capsules in a quantity equal to 400 mg mesalazine. The results obtained with the dissolution test on the so obtained capsules are reported in Table 17.

TABLE 17

| Time | Medium | % dissolution |
|---|---|---|
| 2$^{nd}$ hour | HCl 0.1N | 0.2% |
| 3$^{rd}$ hour | Tampon pH 6.0 | 28.1% |
| 4$^{th}$ hour | Tampon pH 6.5 | 68.0% |
| 6$^{th}$ hour | Tampon pH 7.0 | 100% |

EXAMPLE 12

The granulates obtained in the examples 8.1, 8.2 and 8.3 have been lubricated with 1% magnesium stearate and then pressed in the ratio 1:1:1 with oval punches having a length of 18 mm and a width of 8.6 mm utilizing a three layer tableting machine. The three granulates have been pressed in sequence to obtain tablets having an average weight of about 630 mg. In particular, it has been pressed first the granulate of Example 8.2, then that of Example 8.1 and finally that of Example 8.3. 1 Kg of the so obtained tablets has been then film-coated in a rotating pan with 800 g of an ethanolic solution containing 7% of Eudragit L, 11 g of diethylphtalate and 10 g of stearic acid.

The film-coating of the tablets has been stopped after having reached a weight increase of 45 mg per each tablet.

The results of the dissolution test of the so obtained tablets are reported in Table 18.

TABLE 18

| Time | Medium | % dissolution |
|---|---|---|
| 2$^{nd}$ hour | HCl 0.1N | 2.7% |
| 3$^{rd}$ hour | Tampon pH 6.0 | 32.1% |
| 4$^{th}$ hour | Tampon pH 6.5 | 60.8% |
| 6$^{th}$ hour | Tampon pH 7.0 | 99.7% |

EXAMPLE 13

The clinical evaluation has been conducted administering the formulation of Example 2.4 in comparison with commercial formulations of mesalazine (Asacol® and Claversal®). Twelve healthy subjects having an average age of 41.3 years (between 20.2 and 71.4) have been treated, 4 per group, according to the following scheme:

| Drug | Mesalazine per dose | Active ingredient mesalazine per day |
|---|---|---|
| Asacol ® tablets | 400 mg | 1200 mg |
| Claversal ® tablets | 500 mg | 1500 mg |
| Formulation of example 2.4 | 400 mg | 1200 mg |

The treatment has lasted 8 days. On the 5$^{th}$, 6$^{th}$ and 7$^{th}$ day of treatment 7.5 mg of sodium picosulfate have been administered to the patients to facilitate the intestinal washing. The last dose has been administered on the 8$^{th}$ day at 6.00 A.M. The patients have neither eaten nor drunk up to 9.00 A.M., and have been submitted to an intestinal washing through intake of a suitable dose of polyethylene glycol. After each liter of polyethylene glycol solution the patients have taken orally 5 mg of metoclopramide. For the complete intestinal cleaning 3 l solution were needed.

The ileoscopy has been carried out between 2.00 P.M. and 3.00 P.M., after sedative analgia. The biopsies have been carried out according to this order:

two adjacent samples for the terminal ileum and the cecal ileum valve;
a sample in the zones indicated in Table 19.

The biopsic fragments have been immediately weighed and frozen in liquid nitrogen, then kept at −80° C. Such procedure has been carried out within 30 minutes from the sample collection. The mesalazine content has been determined in ng/mg of humid weight through HPLC. The results are illustrated in the following Table 19, where the quantity of mesalazine, in ng/mg, noticed in each analyzed region, is reported. From Table 19 it turns out that the formulation of this invention allows to obtain more homogeneous tissue concentrations of mesalazine than those obtained with the reference formulations, enabling, therefore, the active ingredient to perform its activity in all anatomical areas.

TABLE 19

| Product | ILE | ICV | CAE | ASC | HEP | TRA | SPL | DES | SIG | REC | Average |
|---|---|---|---|---|---|---|---|---|---|---|---|
| Asacol ® | 468.1 | 551.4 | 503.7 | 362.2 | 230.4 | 313.3 | 296.4 | 121.6 | 115.2 | 106.4 | 306.87 |
| Claversal ® | 171.5 | 107.4 | 97.1 | 116.4 | 80.3 | 123.7 | 104.6 | 105.1 | 80.7 | 90.7 | 107.75 |
| Formulation of example 6 | 321.4 | 380.3 | 390.8 | 360.8 | 290.4 | 263.6 | 220.1 | 180.6 | 140.3 | 110.2 | 265.85 |

Legend:
ILE = terminal ileum
ICV = cecal ileum valve
CAE = cecum
ASC = ascending colon
HEP = hepatic flexure
TRA = transverse colon
SPL = splenic flexure
DES = descending colon
SIG = sigmoid colon
REC = rectum

EXAMPLE 14

The comparative bioavailability of the formulation referred to in example 2.4, test preparation 500 mg, has been investigated in a single dose, crossover trial versus a reference product of the same strength, already marketed.

The investigational formulations have been administered to 12 healthy male volunteers with a wash-out period from 7 to 14 days.

The study showed that serum concentrations of test preparation as compared to those of the reference product:
1) could be detected about 0,5–1 hour earlier;
2) were all lower and clearly more homogeneous;
3) the curves showed a profile without peaks.

As in the blood only the part of the drug that does not exert any therapeutic activity is detected, the above data prove that the available drug in the sites of action in the intestinal lumen is more elevated and in more constant concentrations.

The invention claimed is:

1. A pharmaceutical formulation for multiphasic release of an active ingredient for treating inflammatory bowel disease comprising: a plurality of portions of the active ingredient, the plurality of active ingredient portions being an effective amount sufficient to treat inflammatory bowel disease, the formulation having at least three coated active ingredient portions, a first portion having a coating soluble starting from a pH of 6, a second portion having a coating soluble starting from a pH of 6.5 and a third portion having a coating soluble starting from a pH of 7, such that each active ingredient portion is released starting at a pH corresponding to the solubility of the coating thereon.

2. The pharmaceutical formulation according to claim 1 wherein the first portion comprises 10 to 60% of the formulation, the second portion comprises from 10 to 60% of the formulation and the third portion comprises from 10 to 60% of the formulation.

3. The pharmaceutical formulation according to claim 1 wherein the plurality of active ingredient portions are in a form selected from the group consisting of microtablets, tablets, granules, microgranules, pellets and combinations thereof.

4. The pharmaceutical formulation according to claim 1 wherein the formulation is in a form of a multilayer tablet.

5. The pharmaceutical formulation according to claim 1 wherein at least one coated active ingredient portion is in a unitary form selected from the group consisting of a tablet, a layer and a microtablet, and wherein the unitary form further comprises a second coating thereon, the second coating containing from 5–35% of the same coating as the at least one coated active ingredient portion, from 0 to 10% of a fatty acid having from 12–20 carbon atoms and from 0 to 10% of a pharmaceutically acceptable plasticizer.

6. The pharmaceutical formulation according to claim 1 wherein the at least one coating soluble starting at a pH of 6 is selected from the group consisting of poly(methacrylic-co-methyl methacrylate), 1:1, 135,000 MW, cellulose acetatephtalate, hydroxypropylmethylcellulosephtalate, hydroxypropylmethylcelluloseacetatesuccinate type L and mixtures thereof.

7. The pharmaceutical formulation according to claim 1 wherein the at least one coating soluble starting at a pH of 6.5 is selected from the group consisting of poly(methacrylic acid-co-methyl methacrylate), 1:1, 135,000 MW, Hydroxypropylmethylcellulosephtalate, Hydroxypropylmethylcelluloseacetatesuccinate type L in a mixture 1:1 with poly (methacrylic acid-co- methylmethacralate), 1:2, 135,000 MW, and mixtures thereof.

8. The pharmaceutical formulation according to claim 1 wherein the at least one coating soluble starting at a pH of 7 is selected from the group consisting of poly(methacrylic acid-co-methacrylate), 1:2, 135,000 MW, poly(methylacrylate-co- methyl methacrylate-co-trimethacrylic acid), 7:3:1, 400,000 MW, or Hydroxypropylmethylcellulosephtalate type M, and mixtures thereof.

9. The pharmaceutical formulation according to claim 1 wherein the first coated portion comprises 30–35% of the formulation, the second coated portion comprises 30 to 35% of the formulation and the third coated portion comprises 30 to 35% of the formulation.

* * * * *